(12) United States Patent
Takagi et al.

(10) Patent No.: US 7,038,021 B2
(45) Date of Patent: May 2, 2006

(54) ANTI-DIOXINS MONOCLONAL ANTIBODY SUITABLE FOR ASSAYING DIOXINS IN ENVIRONMENT AND HYBRIDOMA PRODUCING THE SAME

(75) Inventors: Yoko Takagi, Kyoto (JP); Kazuyuki Sawadaishi, Kyoto (JP); Chiwa Kataoka, Kyoto (JP)

(73) Assignee: Kyoto Electronics Manufacturing Co., Ltd., Kyoto (JP)

( * ) Notice: Subject to any disclaimer, the term of this patent is extended or adjusted under 35 U.S.C. 154(b) by 49 days.

(21) Appl. No.: 10/885,229

(22) Filed: Jul. 7, 2004

(65) Prior Publication Data

US 2005/0153378 A1     Jul. 14, 2005

(30) Foreign Application Priority Data

Jan. 8, 2004   (JP) ............................ P2004-003234

(51) Int. Cl.
*C07K 16/00* (2006.01)
*C12N 5/20* (2006.01)
*G01N 33/53* (2006.01)
*G01N 33/531* (2006.01)
*A01N 43/28* (2006.01)

(52) U.S. Cl. .................. 530/388.9; 530/405; 530/809; 435/70.21; 435/961; 435/FOR. 215; 435/FOR. 218; 435/FOR. 231; 435/7.93; 435/7.94; 435/7.95; 436/548; 436/815; 514/454

(58) Field of Classification Search ............ 530/388.9, 530/405, 809; 435/70.21, 961, FOR. 215, 435/FOR. 218, FOR. 231, 7.93–7.95; 436/548, 436/815; 514/454

See application file for complete search history.

(56) References Cited

U.S. PATENT DOCUMENTS 4,798,807 A    1/1989  Vanderlaan et al. ..... 530/388.9

FOREIGN PATENT DOCUMENTS

| JP | 2002-119279 | 4/2002 |
| JP | 2002-189027 | 7/2002 |
| JP | 2002-228660 | 8/2002 |
| JP | 2003-098173 | 4/2003 |

OTHER PUBLICATIONS

Takasuga, T., et al, 11th Symposium on Environmental Chemistry Program and Abstracts, p. 136 (2002).
Fujihira, H., et al, Enfironmental Solution Technology, vol. 2, No. 5, p. 63 (2003).

*Primary Examiner*—Long V. Le
*Assistant Examiner*—Shafiqu Haq
(74) *Attorney, Agent, or Firm*—Bacon & Thomas, PLLC

(57) ABSTRACT

The object of present invention is to provide an immunoassay for dioxins which can rapidly and simply afford measured values having a good correlation with analytical values of dioxins by the official method (GC/MS method). The above object is achieved by using the monoclonal antibody of the present invention having not only a reactivity with the indicator isomer among 17 kinds of PCDDs and PCDFs each having a predetermined WHO-TEF value, but also a high cross-reactivity with several kinds of dioxin isomers having five or six chlorine atoms which contribute largely to a TEQ value, and also having a stable reactivity with the antigens in a measuring solvent.

5 Claims, 2 Drawing Sheets

Standard curve of anti-dioxins monoclonal antibody

Correlation between the results measured using the present antibody (ELISA values) and GC/MS values

ANTI-DIOXINS MONOCLONAL ANTIBODY SUITABLE FOR ASSAYING DIOXINS IN ENVIRONMENT AND HYBRIDOMA PRODUCING THE SAME

TECHNICAL FIELD

The present invention relates to an assay for determining dioxins in the environment. More particularly, the present invention relates to a monoclonal antibody having a high affinity, in particular, for dioxin isomers having five or six chlorine atoms, which contribute largely to a TEQ value, among dioxins each having a predetermined WHO-TEF value, a hybridoma cell line producing said monoclonal antibody, and an immunoassay for determining the amount of dioxins present in the environment using said monoclonal antibody.

The present invention also relates to a phenoxathiin derivative useful as an immunogen in preparing said antibody, as a compound for immobilization of said antibody or a compound (competitor) for competition with said dioxins in an immunoassay, or as a standard substance in an assay system, and a process for preparing said derivative.

BACKGROUND ART

The environmental pollution by internal secretion-disturbing substances becomes serious problems in the atmosphere, incineration ashes, exhaust gas, drain, foods, marine products, soil and the like, and research and investigation have been made on the influences of the environmental pollution on human being and the other organisms, not only in Japan but also many countries of the world. In particular, it is suspected that dioxins lastingly influence an ecological system of human being and the other organisms. Accordingly, investigation of polluted conditions, elucidation of exposure conditions to human being and the other organisms and of intake routes as well as development of a simple monitoring method which can be used rapidly and at many points in polluted facilities, polluted locations and exhaust sources of dioxins have been carried out.

The term "dioxins" is a comprehensive term including dioxins comprised of 75 kinds of polychlorodibenzo-p-dioxins (PCDDs) and 135 kinds of polychlorodibenzofurans (PCDFs) as well as coplanar polychlorobiphenyls, and therefore, there are many structural isomers (they may be referred to as "dioxin isomers" collectively in the specification). The relative toxicity of each dioxin isomer, when assuming the toxicity of 2,3,7,8-tetrachlorodibenzo-p-dioxin (2,3,7,8-TCDD) having the highest toxicity among the above isomers is 1, is shown as the Toxic Equivalency Factor (TEF) by the World Health Organization (WHO), and analysis of dioxins in samples is carried out using 7 kinds of PCDDs and 10 kinds of PCDFs having toxicity values. Thus, the actually determined concentration of each isomer is multiplied by the corresponding TEF value, and the sum total of the values obtained for all the isomers is calculated as the 2,3,7,8-TCDD Toxic Equivalent quantity (TEQ). The TEQ values are used as analytical values of the dioxins.

Also, of polychlorobiphenyls (PCBs) previously known as pollutants in the environment, totally 12 kinds of coplanar PCBs including 4 kinds of non-ortho PCBs and 8 kinds of mono-ortho PCBs have been measured as dioxins, because they show biological effects similar to those of dioxins.

Previously, the determination of dioxins has been carried out by measuring the above 17 kinds of dioxin isomers, by high-resolution gas chromatography/mass spectrometry (GC/MS method) using an expensive analytical instrument, and then calculating the TEQ value from the measured values. However, the GC/MS method needs removal of interfering substances contained in samples, and therefore, a multi-stage of complicated cleanup procedures, skilled analyzers and so on. Also, the method needs much time for obtaining and analyzing the data, and therefore, the use of the method is limited to an analysis in a particular analytical facility. On the other hand, due to the recent innovative progress of investigations, there is a tendency to analyze internal secretion-disturbing substances by a biological technique. Thus, attention is paid to a bioassay, a receptor-binding assay based on biological samples, an immunoassay and the like, for the reason that they are suitable for rapid and simple measurement of samples from the environment containing enormous kinds of dioxin isomers, and they have been developed intensively. In application to the analysis of samples from the environment, however, there arise problems such as deviation from analytical values obtained by the official method (GC/MS method) and lack of reproducibility of a measuring system. Accordingly, it is desired to develop a simple analytical method suitable for measurement of samples from the environment.

Recently proposed is an idea that a total dioxin amount (TEQ) is simply determined by measurement of a particular indicator isomer. In a wide range of samples, for example, samples from the environment such as soil, mud, atmosphere, water, exhaust gas and ash, samples from a living body such as mother's milk and blood as well as marine products, foods and the like, it has been proved that the amount of 2,3,4,7,8-pentachlorodibenzofuran (2,3,4,7,8-PeCDF), which is one of dioxin isomers each having a predetermined TEF value has a very high correlation with the TEQ value (non-patent reference 1). In view of the report, the present inventors investigated a method of determining dioxins using the indicator isomer as a target, developed recombinant antibodies having a high specificity to 2,3,4,7,8-PeCDF, and filed a patent application directed to the subject matters (Japanese Patent Application No. 2003-091663). However, it was found that an antibody having not only a reactivity with the indicator isomer but also a cross-reactivity with plural dioxin isomers which contribute largely to a TEQ value is needed in order to obtain a measuring method having a higher correlation with samples from the environment, and that the use of the antibody provides measured values having a higher correlation with GC/MS values.

Among biological techniques for analysis of dioxins, an attempt to quantifying the dioxins by an immunochemical technique utilizing an antibody is made, for example, in patent reference 1. Thus, the reference discloses a method for detecting dioxins contained in samples from a living body such as human blood and mother's milk by preparing and using a monoclonal antibody having a high affinity for 2,3,7,8-TCDD. Also, patent reference 2 discloses a method for deducing an amount of dioxins present in samples using a few antibodies having a highest affinity for 2,3,7,8-TCDD and also having a cross-reactivity with the other plural isomers. In these references, however, there is no sufficient description as to monoclonal antibodies recognizing dioxins having five or six chlorine atoms as well as measuring methods using said monoclonal antibodies which methods have a correlation with the total dioxin amount (TEQ) in samples from the environment. Thus, these references fail to describe a concrete practice of a measuring method for samples from the environment.

Furthermore, patent reference 3 discloses a method for determining dioxins in soil or mud using a polyclonal antibody having a high affinity for dioxins having eight chlorine atoms. However, this reference does not show a definite correlation between the values measured using the antibody and the GC/MS values measured by instrumental analysis, for dioxins having eight chlorine atoms in samples.

On the other hand, non-patent reference 2 discloses an antibody which shows a cross-reactivity, when assuming the reactivity with 1,2,3,7,8-PeCDF is 100%, of 39.8% with 1,2,3,7,8,9-HxCDD, of 45.9% with 1,2,3,4,7,8-HxCDF, of 36.6% with 1,2,3,6,7,8-HxCDF, of 42.7% with 1,2,3,7,8,9-HxCDF, and of 43.8% with 2,3,4,6,7,8-HxCDF, among 17 kinds of PCDDs and PCDFs each having a predetermined WHO-TEF value. Thus, this reference discloses an antibody having a broad cross-reactivity with dioxins, which shows about 35% to 45% of a cross-reactivity with all PCDFs having six chlorine atoms and one PCDD having six chlorine atoms and also shows about 10% of a reactivity with the other dioxin isomers each having a TEF value. Also, the reference reports that a certain correlation can be seen between the values measured using said antibody for samples from the environment and the GC/MS values.

Non-patent reference 1: Takasuga et al., 11th Symposium on Environmental Chemistry, Program and Abstracts, p. 136, 2002;

Non-patent reference 2: Fujihira et al., Environmental Solution Technology, Vol. 2, No. 5, p. 63, 2003;

Patent reference 1: JP-A-2002-228660;

Patent reference 2: JP-A-2002-119279;

Patent reference 3: JP-A-2003-098173.

DISCLOSURE OF INVENTION (Technical Problems to be Solved by the Invention)

An object of the present invention was to provide an immunoassay for dioxins which can rapidly and simply afford measured values having a good correlation with analytical values of the dioxins by the official method (GC/MS method).

Another object of the present invention was to provide, for the achievement of the above object, a monoclonal antibody having not only a reactivity with the indicator isomer among 17 kinds of PCDDs and PCDFs each having a predetermined WHO-TEF value, but also a high cross-reactivity with several kinds of dioxin isomers having five or six chlorine atoms which contribute largely to a TEQ value, and also having a stable reactivity with the antigens in a measuring solvent.

(Means for Solving the Problems)

In preparing a monoclonal antibody against a low molecular compound such as dioxins, in general, it is difficult to induce an immune response when inoculating an animal with the compound. Accordingly, immunization is carried out using a hapten antigen of which an immunogenicity is enhanced by binding the targeted antigen to a high molecular compound such as proteins or polysaccharides to form a conjugate. In addition, the dioxins are problematic in terms of a strong toxicity such as an immune suppression action for organisms and have a disadvantage of a low handling easiness due to a hard solubility in water. The present inventors synthesized phenoxathiin derivatives (I-1 and I-2) which have a reduced toxicity as compared with the dioxins, a high handling easiness due to a high solubility in water, and a structure similar to that of the dioxins, prepared conjugates (II-1 and II-2) of the derivatives with a protein through a spacer, and immunized an animal using the conjugates as an immunogen. Subsequently, antibody-producing cells from the immunized animal were fused with myeloma cells to prepare hybridoma cells. Next, using II-1 and II-2 as an immobilized antigen in the presence of an organic solvent, hybridoma cells were obtained which produce an antibody having a specificity to targeted dioxin isomers. Also, the selection of specific hybridoma cells was facilitated by simultaneous use of phenoxathiin derivatives I-1 and I-2 for the screening, and an antibody allowing an antigen-antibody reaction in a solvent was obtained by screening in the presence of an organic solvent such as DMSO. Furthermore, the desired immunoassay was established using the antibody.

(Advantageous Effects over the Prior Art)

The monoclonal antibody of the present invention is not an antibody having a broad cross-reactivity with dioxin isomers as shown in non-patent reference 2, but is an antibody having a cross-reactivity with the indicator isomer and several kinds of dioxin isomers having five or six chlorine atoms which contribute largely to a TEQ value, among 17 kinds of dioxin isomers each having a predetermined TEF value. By using the antibody, it is possible to avoid laborious analysis of dioxins by the prior official method (GC/MS method), and to construct an immunoassay for dioxins which can afford measured values having a good correlation with analytical values of the dioxins by the official method, rapidly and simply, and also stably and in a high sensitivity in the presence of an organic solvent. The assay allows, for example, simple analysis and monitoring of dioxins in samples from the environment.

BEST MODE FOR CARRYING OUT THE INVENTION

Figure 1:
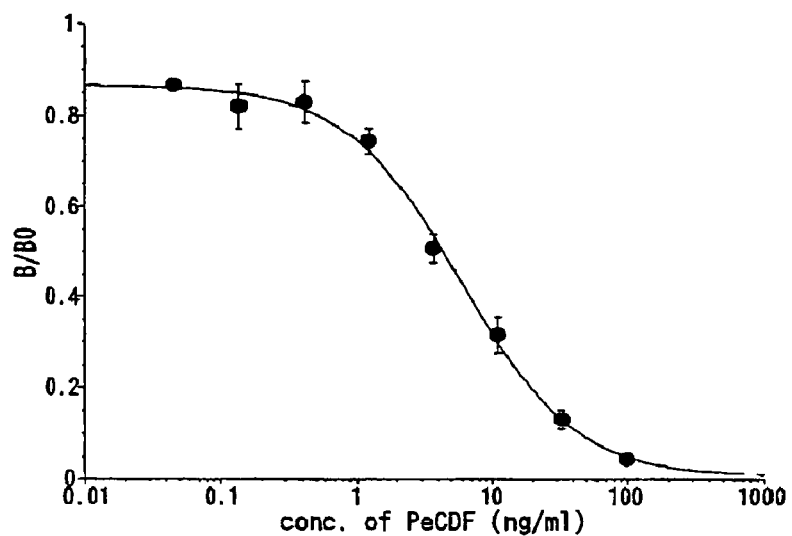
FIG. 1 is a graph showing a standard curve of the reaction of the monoclonal antibody of the present invention with an antigen prepared by an indirect competitive assay.

The present inventors found that hybridoma cells producing the desired anti-dioxins monoclonal antibody can be obtained by binding a phenoxathiin derivative (as a hapten) of the following general formula (I):

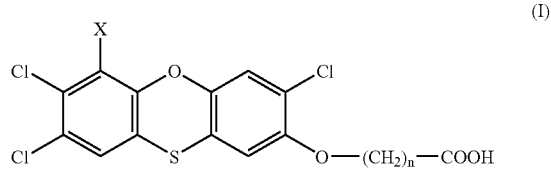

wherein X is a hydrogen atom or a chlorine atom, and n is an integer of 2 to 9, to a carrier protein, immunizing an animal using the resulting conjugate as an immunogen, and then fusing antibody-producing cells from the immunized animal and myeloma cells.

The phenoxathiin derivatives of the above general formula (I) can be prepared, for example, according to the following reaction scheme:

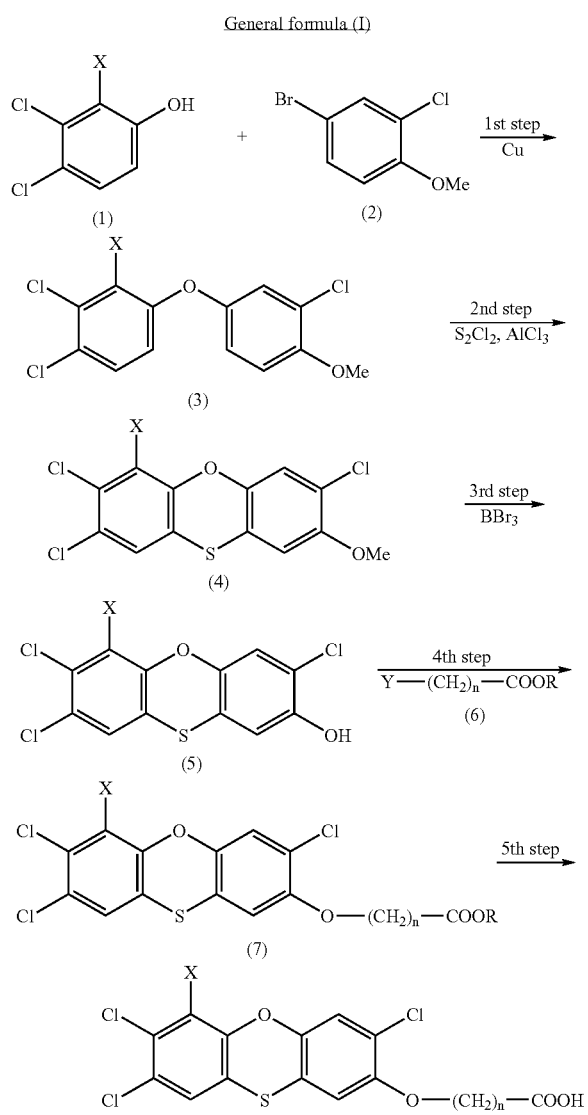

General formula (I)

The phenoxathiin derivatives prepared as described above may be bound to a carrier protein to obtain a conjugate which can be used as an immunogen. The carrier protein includes bovine albumin, ovoalbumin, myoglobin, keyhole limpet hemocyanin and the like. The phenoxathiin derivatives can be bound to the carrier protein as follows. Thus, the carboxyl group of the phenoxathiin derivatives is firstly converted into an active ester group by the condensation reaction with N-hydroxysuccinimide, for example. The active ester derivative is then reacted with an amino group of the carrier protein according to a conventional method to obtain the desired conjugate.

The conjugate prepared as described above is then used as an immunogen to immunize an animal. The conjugate is administered to an animal after emulsifying it by mixing with an adjuvant. Animals to be immunized may be, for example, mice, rats, rabbits or goats. The immunization may be carried out by administering 0.5 to 10 μg of the immunogen per g of body weight into the peritoneal cavity of an animal, 3 to 12 times at intervals of 2 to 3 weeks.

The preparation of a monoclonal antibody may be carried out, for example, according to the method of Kohler G. and Milstein C. (Nature, 256, 495–7 (1975)).

After three days from the final immunization, the antibody-producing cells are recovered from the immunized animal. The antibody-producing cells may be, for example, spleen cells or lymph node-derived B cells. The antibody-producing cells are fused with myeloma cells according to a conventional method. The myeloma cells may be a cell line derived from mice, rats or humans. The cell fusion method may be, for example, a polyethylene glycol method or an electrical fusion method.

The selection of hybridomas obtained by the cell fusion may be carried out, for example, by radioimmunoassay (RIA), enzyme immunoassay (ELISA) or fluoroimmunoassay (FIA). Thus, dioxins, phenoxathiins and conjugate compounds of phenoxathiin derivatives with a carrier protein are reacted with a supernatant of hybridoma cultures, and wells containing hybridomas which produce an anti-dioxins antibody are selected. The hybridomas in the wells are then mono-cloned by a limiting dilution method to establish antibody-producing hybridoma cells.

The selection of hybridomas is carried out by reacting an antigen with an antibody in a short time (10 to 30 minutes) in an aqueous solution containing an organic solvent used in an immunoassay. The aqueous solution containing an organic solvent may be, for example, an aqueous solution containing 10 to 40%, preferably 20 to 30% of DMSO, methanol or ethanol. By doing so, antibody-producing hybridomas are selected which show a stable, high reactivity with an antigen even in an aqueous solution containing an organic solvent.

The preparation of a monoclonal antibody on a large scale can be carried out, for example, in the following manner. An established antibody-producing hybridoma cell line is implanted into the peritoneal cavity of a mouse previously administered with pristan (2,6,10,14-tetramethylpentadecan), and the ascites fluid of the mouse containing the monoclonal antibody is recovered after 10 to 14 days from the implantation. The monoclonal antibody can be easily recovered from the ascites fluid, for example, by ammonium sulfate precipitation, ion-exchange chromatography, or affinity chromatography.

It is possible to use the monoclonal antibody of the present invention thus obtained, for example, in an immunological detection method described in the prior art (JP-A-2002-189027) or in an immunoassay by a non-competitive or competitive method (indirect or direct competitive method), and to measure dioxins in samples. Such a measuring method includes, for example, radioimmunoassay (RIA), enzyme immunoassay (ELISA), and fluoroimmunoassay (FIA).

The measurement of dioxins is carried out, for example, by (a) subjecting a sample containing dioxins in an aqueous solution containing an organic solvent and the monoclonal antibody of the present invention to an antigen-antibody reaction, and (b) detecting the dioxins bound to the antibody or the antibody not reacted with the dioxins. The organic solvent includes DMSO, methanol, ethanol and the like, and may be present in the aqueous solution in a concentration of 10 to 40%, preferably 20 to 30%.

Also, the present monoclonal antibody may be used in a system using a transducer such as a SPR (surface plasmon) sensor and a QCM (crystal oscillator) sensor, an optical sensor and an electrochemical sensor as well as in an immunological sensor in which an antigen or antibody is immobilized on surfaces of functional sites. On the other hand, it is also possible to use the present monoclonal antibody for removing dioxins by immobilizing the antibody on a suitable carrier.

The monoclonal antibody of the present invention may be used according to the procedures usually used in these methods.

In addition, if it is necessary to label the antibody and the dioxin derivative supplied to measuring systems, labels well known in the art such as radioisotopes, enzymes and fluorescent substances may be used in a conventional manner.

EXAMPLES

The present invention is illustrated more specifically based on the following examples, but it is not limited thereto and rather includes any conventional alteration and modification therefor carried out in the art.

Example 1

Synthesis of Phenoxathiin Derivatives (1) Synthesis of 6-(3,7,8-trichlorophenoxathiin-2-yloxy)hexanoic acid 3,4-Dichlorophenol was dissolved in methanol, an equal amount of potassium hydroxide was added to the solution, and the solvent was then distilled off. Toluene was added to the residue, the solvent was removed under a reduced pressure, and the residue was then dried at 100° C. for one hour under a reduced pressure. To this were added 4-bromo-2-chloroanisole and cuprous chloride and anhydrous pyridine, and the mixture was stirred for 24 hours under reflux with heating. The solvent was removed under a reduced pressure, chloroform and water were added to the residue, and the layers were then separated. The organic layer was washed sequentially with 1N hydrochloric acid and water, and the solvent was then removed under a reduced pressure. The residue was purified by silica gel chromatography to obtain 3,3',4-trichloro-4'-methoxydiphenyl ether.

The ether compound was dissolved in 1,1,2,2-tetrachloroethane, anhydrous aluminium chloride and sulfur chloride were added to the solution, and the mixture was reacted at 80° C. for one hour with stirring. After completion of the reaction, water was added to the mixture. The mixture was then extracted with chloroform, and the solvent of the organic phase was removed under a reduced pressure. The residue was purified by silica gel chromatography to obtain 2,3,7-trichloro-8-methoxyphenoxathiin.

Next, the resulting compound was dissolved in anhydrous dichloromethane, a solution of boron tribromide in dichloromethane was added to the former solution, and the mixture was stirred overnight at room temperature. The reaction solution was poured on ice, the mixture was extracted with dichloromethane, and the solvent of the organic phase was removed under a reduced pressure. The residue was purified by silica gel chromatography to obtain 3,7,8-trichlorophenoxathiin-2-ol.

The resulting compound was dissolved in dimethylformamide, anhydrous potassium carbonate and ethyl bromohexanoate were added to the solution, and the mixture was stirred overnight at 60° C. The solvent was removed under a reduced pressure, dichloromethane and water were added to the residue, and the layers were separated. The organic layer was washed with water, and the solvent was then removed under a reduced pressure. The residue was dissolved in a mixed solvent of dioxane and methanol, 10N sodium hydroxide was added to the solution with stirring, and the mixture was reacted at room temperature for one hour. The reaction solution was neutralized with hydrochloric acid, the mixture was concentrated under a reduced pressure, and the residue was dissolved by adding chloroform and water thereto. The solution was acidified with hydrochloric acid, and the layers were separated. The organic layer was washed with water, and the solvent was removed under a reduced pressure. The residue was washed with ethanol and recrystallized with ethanol to obtain 6-(3,7,8-trichlorophenoxathiin-2-yloxy)hexanoic acid in an overall yield of 7.5%.

$^1$H-NMR (270 MHz, DMSO-$d_6$): δ 12.01 (br, 1H), 7.67 (s, 1H), 7.24 (s, 1H), 7.13 (s, 1H), 7.09 (s, 1H), 4.01 (t, 2H), 2.23 (t, 2H), 1.72 (m, 2H), 1.57 (m, 2H), 1.42 (m, 2H).

(2) Synthesis of 6-(3,6,7,8-tetrachlorophenoxathiin-2-yloxy)hexanoic acid

Similar procedures were carried out using 2,3,4-trichlorophenol instead of 3,4-dichlorophenol used in the above (1) to obtain 6-(3,6,7,8-tetrachlorophenoxathiin-2-yloxy)hexanoic acid in an overall yield of 4.3%.

$^1$H-NMR (270 MHz, DMSO-$d_6$): δ 12.01 (br, 1H), 7.67 (s, 1H), 7.24 (s, 1H), 7.13 (s, 1H), 4.01 (t, 2H), 2.23 (t, 2H), 1.72 (m, 2H), 1.57 (m, 2H), 1.42 (m, 2H).

The chemical structures of the compounds of Example 1 are shown in Table 1.

TABLE 1

| Hapten | Structure |
|---|---|
| I-1 | [structure: phenoxathiin with Cl substituents and O—(CH$_2$)$_6$—COOH side chain] |
| I-2 | [structure: phenoxathiin with Cl substituents and O—(CH$_2$)$_5$—COOH side chain] |

Example 2

Preparation of Conjugates of Phenoxathiin Derivatives with a Carrier Protein

Two phenoxathiin derivatives synthesized in Example 1 were bound to bovine serum albumin (BSA) as a carrier protein, utilizing the carboxylic acid in said derivatives.

N-Hydroxysuccinimide, 1-ethyl-3-(3-diethylaminopropyl)carbodiimide hydrochloride, and N,N-diisopropylethylamine were added to a solution of 6-(3,7,8-trichlorophenoxathiin-2-yloxy)hexanoic acid (hapten I-1) in dimethylformamide, and the mixture was stirred overnight at room temperature. After completion of the reaction, the reaction solution was concentrated under a reduced pressure, and the residue was extracted with chloroform. The extracted solution was washed with water and then concentrated under a reduced pressure. The residue was purified by silica gel chromatography to obtain N-succinimidyl-6-(3,7,8-trichlorophenoxathiin-2-yloxy)hexanoate.

The resulting compound was dissolved in dimethylsulfoxide (DMSO), the solution was added to a solution of BSA dissolved in 50 mM phosphate buffer (pH 8.0) with stirring under ice-cooling, and the mixture was stirred overnight at room temperature. The reaction solution was added to a Sephadex column equilibrated with PBS (−), and the conjugate of hapten I-1 with BSA was purified by eluting the column with the same buffer.

The conjugate of hapten I-2 with BSA was prepared by carrying out procedures similar to those described above using 6-(3,6,7,8-tetrachlorophenoxathiin-2-yloxy)hexanoic acid (hapten I-2).

The structures of the conjugates of Example 2 are shown in Table 2.

TABLE 2

| Conjugate | Structure |
|---|---|
| II-1 | 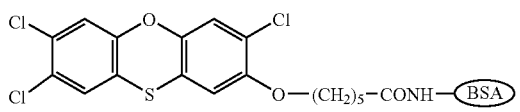 |
| II-2 | 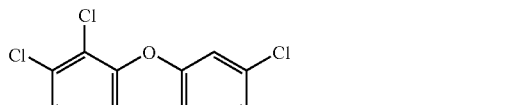 |

Example 3

Preparation of an Anti-dioxins Monoclonal Antibody (1) Immunization of Mouse

Immunization of mouse was carried out using the conjugates of phenoxathiin derivatives (II-1 and II-2) having a reduced toxicity to mouse as an immunogen, and using RAS R-700 (RIBI Co.) as an adjuvant. Thus, a solution of the antigens was thoroughly emulsified by mixing the solution with the adjuvant in a ratio of 1:1 (v/v ratio). The emulsion (200 μl) was then administered into the peritoneal cavity of BALB/c mice (7 to 8 weeks age, male) to immunize the mice. Booster immunizations were carried out at intervals of about 2 to 3 weeks, blood samples were taken from the tail vein after the passage of one week from each booster immunization, and the antibody titer in blood was measured by an ELISA method to observe the change of the antibody titer.

(2) Cell Fusion

Final immunization was carried out by administering II-1 or II-2 into the tail vein of the mice in which a high level production of an antibody against II-1 or II-2 was observed. After 3 days from the final immunization, the spleen was removed from the mice and spleen cells were prepared. Myeloma cells (P3-X63-Ag8.653 or Sp2/O) in a logarithmic growth phase and the spleen cells were mixed in a ratio of 1:5, and the cell fusion was carried out by a polyethylene glycol (PEG) method. The cells after fusion were suspended into a RPMI 1640 medium containing 10% FCS to which HAT (hypoxanthine, aminopterin and thymidine) were added. The suspension was seeded in 96-well culturing plate so that the number of the spleen cells was 1 to $2\times10^5$ cells/well, and cultivation was carried out at 37° C. under 5% $CO_2$.

(3) Screening and Cloning of Antibody-Producing Hybridomas

After 7 to 10 days from the cell fusion, the antibody titer was determined using the supernatant of the culture in the well in which proliferation of a clone was observed. The determination of the antibody titer was carried out by an ELISA method.

(4) Screening of Antibody-Producing Hybridomas (Determination of Antibody Titer)

A solution (50 μl) of II-1 or II-2 diluted with PBS (−) to 0.25 to 1 μg/ml was added to wells of a microtiter plate (Corning Co.), and the plate was allowed to stand at room temperature for one hour to immobilize the conjugates. Also, in order to exclude a clone producing an antibody against the carrier protein, BSA was immobilized to wells and the wells were used as a control. The wells were washed three times with a washing solution [PBS (−) containing 0.05% Tween 20](300 μl). A solution (300 μl) of Block Ace (Yukijirushi Co.) prepared by 4-fold diluting with deionized water was then added to the wells, and the wells were blocked by allowing it to stand at room temperature for 2 hours. The wells were washed three times with the washing solution (300 μl). A solution (25 μl) of 20% DMSO and 0.01% Triton-X100 as well as the supernatant (25 μl) of the culture containing a primary antibody were then added to the wells and mixed in the wells. The wells were allowed to stand at room temperature for 10 to 30 minutes to effect an antigen-antibody reaction.

The wells were washed three times with the washing solution (300 μl). Then, in order to detect the primary antibody which was bound to II-1 or II-2 immobilized onto the plate, a solution (50 μl) of a horseradish peroxidase-labeled anti-mouse IgG (recognizing γ-chain)(KPL Co.) prepared by 3000-fold diluting with a solution of Block Ace 10-fold diluted with deionized water was added to the wells as a solution of a secondary antibody, and reacted at room temperature for one hour. After the wells were again washed three times with the washing solution (300 μl), a solution of 3,3',5,5'-tetramethylbenzidine (TMB)(KPL Co.) was added to the wells and a coloration reaction was effected at room temperature. After 5 to 15 minutes, the reaction was terminated by adding 1 M phosphoric acid (50 μl), and the absorbance at 450 nm was immediately measured using a microplate reader (Multiscan, Labsystems Co.). The difference between the absorbance in the well in which II-1 or II-2 was immobilized and the absorbance in the control well was adopted as a binding activity of a sample antibody against the antigen, and clones showing a high absorbance in the control wells were excluded.

(5) Selection of a Specific Antibody-Producing Clone by an Indirect Competitive Assay According to the method used for determination of the antibody titer, antigen II-1 or II-2 was immobilized onto wells of a microtiter plate and the wells were washed. A solution (300 μl) of Block Ace 4-fold diluted with deionized water was then added to the wells, and the wells were blocked by allowing it to stand at room temperature for 2 hours. The wells were washed three times with the washing solution (300 μl). The supernatant (25 μl) of the culture containing a primary antibody as well as a solution (25 μl) of various concentrations of a phenoxathiin derivative (I-1 or I-2), which is a compound for screening having a structure similar to that of dioxins and having a reduced toxicity, in 20% DMSO and 0.01% Triton-X100, or a solution (25 μl) of various concentrations of dioxins in 20% DMSO and 0.01% Triton-X100, or a solution (25 μl) containing neither the phenoxathiin derivatives nor the dioxins in 20% DMSO and 0.01% Triton-X100 which serves as a control were then added to the wells and mixed in the wells. The wells were allowed to stand at room temperature for 10 to 30 minutes to effect an antigen-antibody reaction.

The wells were washed three times with the washing solution (300 μl). Then, in order to detect the primary antibody which was bound to II-1 or II-2 immobilized onto the plate, a solution (50 μl) of a horseradish peroxidase-labeled anti-mouse IgG (recognizing γ-chain) prepared by 3000-fold diluting with a solution of Block Ace 10-fold diluted with deionized water was added to the wells as a solution of a secondary antibody, and reacted at room temperature for one our. After the wells were again washed three times with the washing solution (300 μl), a TMB solution was added to the wells, and a coloration reaction was effected at room temperature. After 5 to 15 minutes, the reaction was terminated by adding 1 M phosphoric acid (50 µl), and the absorbance at 450 nm was immediately measured using a microplate reader. The ratio (B/B0) of an absorbance value (B) in the well to which one of phenoxathiin derivatives or dioxins was added, to an absorbance value (control OD; B0) in the well to which only a solution of 20% DMSO and 0.01% Triton-X100 was added but neither the phenoxathiin derivatives nor the dioxins were added, was calculated to evaluate the reactivity of the primary antibody. A hybridoma in the well in which a continuously high production of an antibody having a high binding activity against the antigens was recognized was selected, expanded, and cloned by a limiting dilution method.

By the above procedures, hybridoma Dx02-I-1 producing monoclonal antibody Dx02-I-0 which has a high reactivity with II-1 and II-2 and shows a high specificity to dioxins was established. The hybridoma Dx02-I-1 was deposited to International Patent Organism Depositary, National Institute of Advanced Industrial Science and technology (AIST Tsukuba Central 6, 1-1, Higashi 1-Chome Tsukuba-shi, Ibaraki-ken 305-8566 Japan) under the terms of the Budapest Treaty on Dec. 19, 2003, and obtained the accession number of FERM BP-08583.

(6) Large-scale Preparation and Purification of the Monoclonal Antibody

Pristan (2,6,10,14-tetramethylpentadecan; Wako Junyaku Co.) (0.5 ml) was administered into the peritoneal cavity of BALB/c mice, and the mice were bred for 2 to 3 weeks. A culture of monoclonal antibody-producing hybridoma Dx02-I-1 previously maintained in a logarithmic growth phase was recovered and the supernatant was removed from the culture. The hybridoma cells were then diluted with RPMI 1640 not containing FCS to a cell density of $1 \times 10^7$ cells/0.5 ml. The cell solution was injected into the peritoneal cavity of BALB/c mice previously administered with pristan. After 10 to 14 days from the injection, exuded ascites fluid was recovered from the abdomen of the mice using a syringe. The ascites fluid recovered was filtrated through a filter having a pore size of 0.22 µm φ. The filtrate was then purified, according to a conventional method, by affinity chromatography using a protein G-Sepharose column (Amersham Biosciens Co.) to prepare the present monoclonal antibody.

Example 4

Evaluation of Properties of the Monoclonal Antibody (1) Analysis of Isotype

An isotype analysis of the monoclonal antibody Dx02-I-0 produced by the established hybridoma Dx02-I-1 was carried out using II-1 or II-2 as a solid phase antigen and using Mouse Typer Kit (BIO-RAD). As a result, it was found that the H chain is IgG1 and the L chain is κ.

(2) Preparation of a Standard Curve by an Indirect Competitive Assay

According to the indirect competitive assay described above, an experiment investigating inhibition by 2,3,4,7,8-PeCDF was carried out using the purified antibody (Dx02-I-0). II-1 was immobilized onto a microtiter plate at room temperature for one hour, and the plate was washed three Limes with the washing solution (300 µl). A solution (300 µl) of Block Ace prepared by 4-fold diluting with deionized water was then added to the wells, and the wells were blocked at room temperature for 2 hours. The wells were washed three times with the washing solution. Various concentrations of one of dioxins prepared by 3-fold dilution starting from a 100 ng/ml concentration (a solution in 20% DMSO and 0.01% Triton-X100) or a solution (25 µl) of 20% DMSO and 0.01% Triton-X100 not containing any dioxin which serves as a control as well as the primary antibody, i.e. the purified monoclonal antibody (25 µl) were then added to the wells and mixed in the wells. The wells were allowed to stand at room temperature for 10 to 30 minutes to effect an antigen-antibody reaction.

The wells were then washed, and a secondary antibody, i.e. a solution (50 µl) of a horseradish peroxidase-labeled anti-mouse IgG (recognizing γ-chain) prepared by 3000-fold diluting with a solution of Block Ace 10-fold diluted with deionized water was added to the wells, and reacted at room temperature for one hour. After the wells were washed, a TMB solution was added to the wells and a coloration reaction was effected at room temperature. After 5 to 15 minutes, the reaction was terminated by adding 1 M phosphoric acid (50 µl), and the absorbance at 450 nm was immediately measured using a microplate reader. The ratio (B/B0) of an absorbance value (B) in the well to which one of dioxins was added, to control OD (B0) was calculated, and the calculated values were plotted against the concentrations of the added dioxin with single logarithm to obtain a typical sigmoid curve (FIG. 1).

As a result, it was shown that a highly sensitive assay system being able to detect about 1 ng/ml or less of 2,3,4,7,8-PeCDF can be constructed using the monoclonal antibody of the present invention.

(3) Evaluation of Cross-reactivity of the Antibody

Using monoclonal antibody Dx02-I-0, the cross-reactivity with 17 kinds of dioxins each having a toxicity value and 12 kinds of coplanar PCBs was evaluated by an indirect competitive assay. II-1 (50 µl) was added to wells in a microtiter plate, and the wells were allowed to stand at room temperature for one hour and then washed. After the wells were blocked, various concentrations of one of dioxins (25 µl) dissolved in 20% DMSO and 0.01% Triton-X100 or a solution (25 µl) of 20% DMSO and 0.01% Triton-X100 not containing any dioxin which serves as a control as well as a solution (25 µl) of the antibody diluted with 0.01 to 0.1% BSA were added to the wells in the plate, and reacted at room temperature for 10 to 30 minutes.

Then, a coloration reaction was effected using a secondary antibody against the antibody bound to the solid phase, i.e. a peroxidase-labeled anti-mouse IgG antibody (recognizing γ-chain) as well as TMB. After the enzyme reaction was terminated, the absorbance at 450 nm was immediately measured. The B/B0 values were plotted for various dioxins, $IC_{50}$ values were calculated from the resulting figures, and the cross-reactivity of the antibody was obtained from these values (Table 3).

TABLE 3

Cross-reactivity of monoclonal antibody Dx02-I-0

| Dxn isomer | No. | TEF | $IC_{50}$ (ng/ml) | Cross-reactivity |
|---|---|---|---|---|
| 2,3,7,8-TeCDD | D48 | 1 | 7.2 | 13 |
| 1,2,3,7,8-PeCDD | D54 | 1 | 29.6 | 3 |
| 1,2,3,4,7,8-HxCDD | D66 | 0.1 | >100 | <1 |
| 1,2,3,6,7,8-HxCDD | D67 | 0.1 | 0.984 | 93 |
| 1,2,3,7,8,9-HxCDD | D70 | 0.1 | 1.06 | 86 |
| 1,2,3,4,6,7,8-HpCDD | D73 | 0.01 | >100 | <1 |
| OCDD | D75 | 0.0001 | >100 | <1 |
| 2,3,7,8-TeCDF | F83 | 0.1 | 12.3 | 7 |
| 1,2,3,7,8-PeCDF | F94 | 0.05 | 0.915 | 100 |
| 2,3,4,7,8-PeCDF | F114 | 0.5 | 5.86 | 16 |
| 1,2,3,4,7,8-HxCDF | F118 | 0.1 | >100 | <1 |
| 1,2,3,6,7,8-HxCDF | F121 | 0.1 | >100 | <1 |
| 1,2,3,7,8,9-HxCDF | F124 | 0.1 | 35.5 | 3 |
| 2,3,4,6,7,8-HxCDF | F130 | 0.1 | 0.989 | 93 |

TABLE 3-continued

Cross-reactivity of monoclonal antibody Dx02-I-0

| Dxn isomer | No. | TEF | IC$_{50}$ (ng/ml) | Cross-reactivity |
|---|---|---|---|---|
| 1,2,3,4,6,7,8-HpCDF | F131 | 0.01 | >100 | <1 |
| 1,2,3,4,7,8,9-HpCDF | F134 | 0.01 | 2.67 | 34 |
| OCDF | F135 | 0.0001 | >100 | <1 |
| 3,4,4',5-TeCB | #81 | 0.0001 | >100 | <1 |
| 3,3',4,4'-TeCB | #77 | 0.0001 | >100 | <1 |
| 3,3',4,4',5-PeCB | #126 | 0.1 | 53.7 | 2 |
| 3,3',4,4',5,5'-HxCB | #169 | 0.01 | 62.9 | 1 |
| 2',3,4,4',5-PeCB | #123 | 0.0001 | >100 | <1 |
| 2,3',4,4',5-PeCB | #118 | 0.0001 | >100 | <1 |
| 2,3,3',4,4'-PeCB | #105 | 0.0001 | >100 | <1 |
| 2,3,4,4',5-PeCB | #114 | 0.0005 | >100 | <1 |
| 2,3',4,4',5,5'-HxCB | #167 | 0.00001 | >100 | <1 |
| 2,3,3',4,4',5-HxCB | #156 | 0.0005 | >100 | <1 |
| 2,3,3',4,4',5'-HxCB | #157 | 0.0005 | >100 | <1 |
| 2,3,3',4,4',5,5'-HpCB | #189 | 0.0001 | >100 | <1 |

The antibody used in this experiment showed a high cross-reactivity with dioxin isomers targeted by the present inventors, among several kinds of PCDDs and PCDFs having five or six chlorine atoms, which are considered largely contributory to a TEQ value. Thus, it was found that the antibody shows a reactivity, when assuming the reactivity with 1,2,3,7,8-PeCDF is 100%, of 93% with 1,2,3,6,7,8-HxCDD, of 86% with 1,2,3,7,8,9-HxCDD, and of 93% with 2,3,4,6,7,8-HxCDF, and thus has a very high reactivity with 4 kinds of these dioxin isomers having five or six chlorine atoms. Also, the antibody shows a reactivity of 34% with 1,2,3,4,7,8,9-HpCDF, of 13% with 2,3,7,8-TeCDD, and of 16% with 2,3,4,7,8-PeCDF.

(4) Measurement of Samples from the Environment

Figure 2:
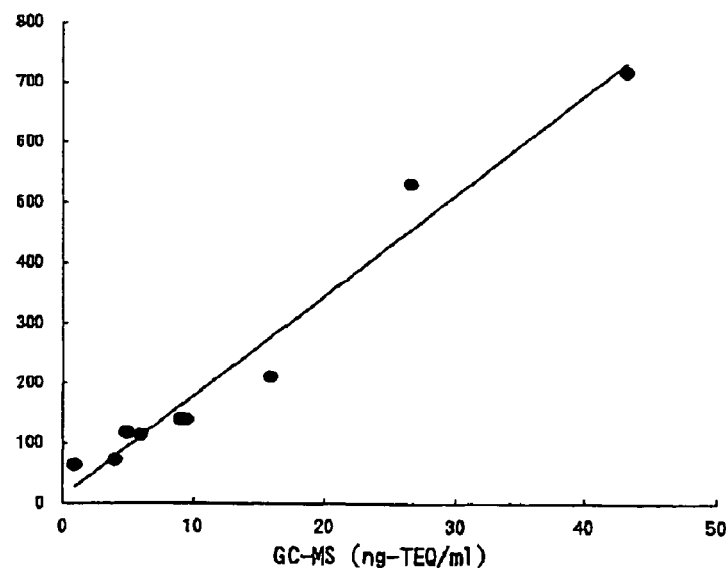
FIG. 2 is a graph showing the correlation between the results obtained by analyzing dioxins in samples from the environment using the monoclonal antibody of the present invention and the results obtained by the GC/MS method.

Using monoclonal antibody Dx02-I-0 obtained according to the present invention, analysis of dioxins was carried out in nine different concentrations of samples from the environment (such as exhaust gas). According to the official method, the samples from the environment were pretreated, DMSO-substituted, and measured by an indirect competitive assay. When the ELISA values were converted into the 2,3,4,7,8-PeCDF values according to the standard curve and the resulting values were plotted against the GC/MS values, a good correlation was obtained (FIG. 2). Thus, it was confirmed that an assay system suitable for analysis of dioxins in samples from the environment can be constructed using this antibody.

(5) Reactivity of Anti-dioxins Monoclonal Antibody Dx02-I-0 in DMSO

According to the method for determining an antibody titer, the reactivity of monoclonal antibody Dx02-I-0 in DMSO was evaluated.

Figure 3:
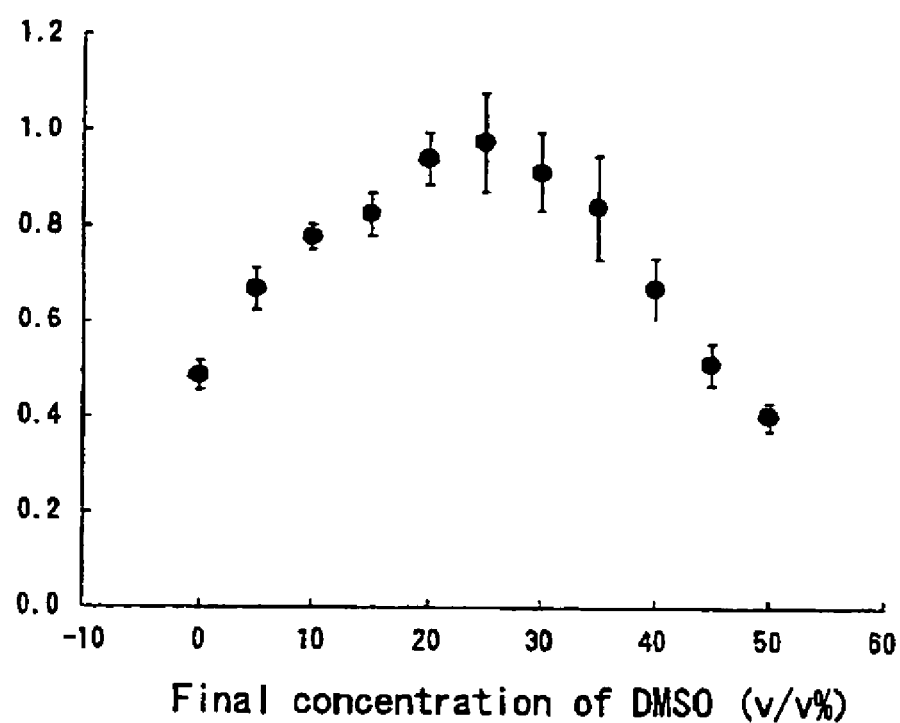
FIG. 3 is a graph showing the reactivity of the monoclonal antibody of the present invention in various concentrations of DMSO.

In this assay system, a sample solution and an antibody solution are reacted in a ratio of 1:1, and this means that the sample solution is 2-fold diluted. As shown in FIG. 3, the reactivity of the antibody with dioxin derivative II-1 reaches its maximum when the final concentration of DMSO is 25%, and rapidly falls when the concentration exceeds 40%. Thus, in monitoring of samples from the environment, for example, the present antibody allows the samples obtained as a DMSO solution to be supplied to an assay system only by 2-fold diluting them. Also, it was found that this assay system allows satisfactory measurement of samples containing a sub-ppb ($10^{-9}$) level of dioxins and is a highly sensitive assay system.

INDUSTRIAL APPLICABILITY

By using the monoclonal antibody of the present invention, it is possible to construct an immunoassay for dioxins. By using the assay, it is possible to avoid laborious analysis of dioxins by the prior official method (GC/MS method), and to afford measured values having a good correlation with analytical values of dioxins by the official method, rapidly and simply, and also stably and in a high sensitivity.

The invention claimed is:

1. Monoclonal antibody Dx02-I-0 having a high affinity for dioxin isomers.

2. An isolated hybridoma cell line Dx02-I-1 producing the monoclonal antibody according to claim 1.

3. A non-competitive or competitive for analyzing the amounts of dioxins (total TEQ value) in a sample, which comprises:
   (a) subjecting a sample containing dioxins and the monoclonal antibody according to claim 1 to an antigen-antibody reaction; and
   (b) measuring the amounts of dioxins bound to the antibody or the amounts of the antibody not reacted with the dioxins.

4. A method for screening and cloning the hybridoma cell line according to claim 2, which comprises reacting a phenoxathiin derivative of the following general formula (I):

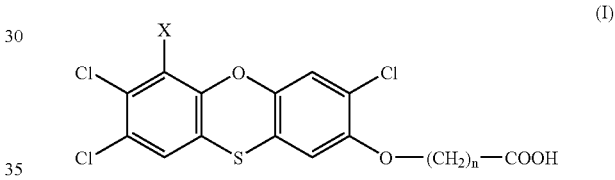

wherein X is a hydrogen atom or a chlorine atom, and n is an integer of 2 to 9, a supernatant from wells containing culture of hybridoma cells, and selecting and cloning the hybridoma cell producing antibody having high binding activity for the phenoxanthiin derivatives.

5. A process for preparing the monoclonal antibody according to claim 1, which comprises immunizing an animal using a conjugate of the following general formula (II):

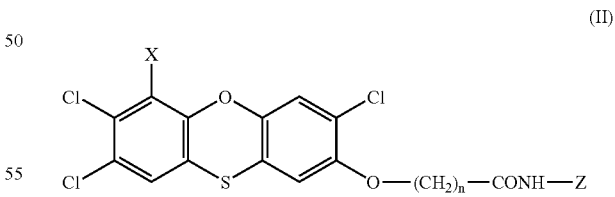

wherein X is a hydrogen atom or a chlorine atom, n is an integer of 2 to 9, and Z is a carrier protein, producing an antibody selectively reacting with dioxins in the body of said animal, fusing antibody-producing cells of said animal with myeloma cells, selecting cloning a hybridoma cell line producing antibody having high binding activity for the phenoxanthiin derivatives according to claim 3, and cultivating said hybridoma cell line.

* * * * *